Dec. 31, 1968 H. C. SWIM ET AL Plant Pat. 2,855
ROSE PLANT
Filed June 20, 1967
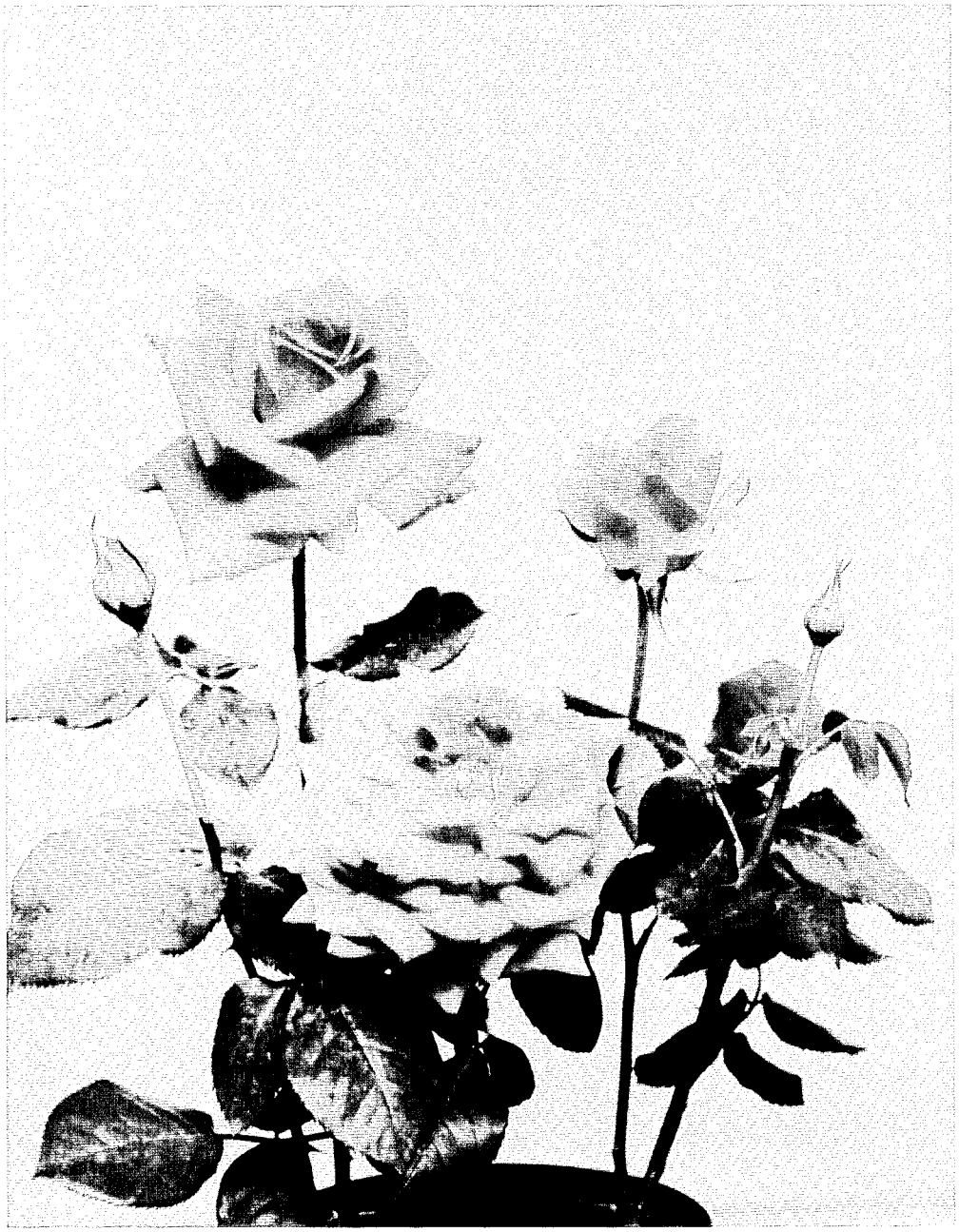

United States Patent Office

Plant Pat. 2,855
Patented Dec. 31, 1968

2,855
ROSE PLANT

Herbert C. Swim, Ontario, and O. L. Weeks, Chino, Calif., assignors, by mesne assignments, to The Conard-Pyle Company, West Grove, Pa., a corporation of Pennsylvania Filed June 20, 1967, Ser. No. 647,572
1 Claim. (Cl. Plt.—19)

This invention relates to a new and distinct variety of rose plant of the grandiflora class.

The plant is of half hardy character, adapted for outdoor cultivation. It is a seedling of the bush type, relatively tall, well adapted for the production of cut flowers and for garden decoration.

The variety was originated by us by crossing Spartan (Plant Patent No. 1,357) as seed parent with an unnamed pollen parent resulting from a cross of Carrousel × Happiness. As a result of this breeding, we have produced a new and improved rose variety shown in various stages of development in the accompanying color photograph, which illustrates new and mature foliage, and various phases of the flower from bud to full-blown maturity.

Some of the unique characteristics of this new rose plant are as follows:

(1) The distinctive two-tone, orange-red color of the flowers;

(2) The high-centered, heavily petaled character of the flowers;

(3) The vigor of the plants and the attendant heavy production of flowers, which is typical of the grandiflora class to which this variety belongs;

(4) The stiff erect character of the stems and neck;

(5) The large quantity of small prickles on the peduncle, and the large size of the prickles on the canes and the branches;

(6) The characteristically rolled-down margins of the leaflets.

We regard these characteristics as comprising major points of difference between the new variety and its parents, and believe that, taken together they distinguish this different variety from all others.

In comparison with the seed parent, Spartan, the following differences may be noted:

(1) Whereas Spartan is classed as a floribunda rose, this new variety belongs to the taller grandiflora class. It is at least twice as tall as Spartan;

(2) Whereas the flowers of the Spartan rose are medium sized, ranging from 3″ to 3½″ in diameter and having approximately thirty petals, the flowers of this new variety are distinctly larger, ranging from 3½″ to 4″ or even more, and have a greater number of petals—from forty to fifty;

(3) Spartan is distinguished by a relatively high fragrance, whereas the new variety has a much milder fragrance;

(4) The stems on this new variety are longer, stiffer and heavier than in the seed parent, and the prickles are substantially larger and heavier;

(5) The flowers of this new variety are considerably darker in color and more heavily pigmented than those of the Spartan rose;

(6) The foliage of this new variety is substantially larger than that of the Spartan plant, but the leaves are not as abundant.

This new variety is distinct from its pollen parent, the unnamed seedling from the cross of Carrousel × Happiness, in the following ways:

(1) Whereas the pollen parent produced a flower of deep red color, this new variety should more accurately be described as having flowers of two-tone orange-red;

(2) Whereas the pollen parent was prone to produce flowers characterized by large greenish vegetative centers, this new variety has never been observed to do this;

(3) Whereas the flowers of the pollen parent were rarely smaller than 4″ in diameter, the flowers of this new variety are seldom much larger than this;

(4) This new variety is far more prolific in the production of flowers than was its pollen parent.

The new variety was asexually reproduced by budding at Chino, Calif. It has not yet been introduced to the trade.

The plant holds its distinguishing characteristics through succeeding propagations. These include a more or less continuous blooming habit and a slight but delicate fragrance. Also, the blooms are free to abundant in quantity, both indoors and in the greenhouse. Furthermore, the flowers are usually borne singly, on strong medium to long stems, although they will occasionally appear in an irregular cluster.

Details with respect to the plant and its bloom are as follows:

*Bud*

The peduncle is medium to long, of heavy caliper, erect and stiff. It is yellowish-green in color, rough, and has numerous prickles.

Before the calyx breaks the bud is of medium to large size. It is short and pointed, with a conspicious neck, and has few if any foliaceous appendages on the surface of the bud. It has slender somewhat spine-like parts extending beyond the tip of the bud for a distance equal to about one-quarter of its length. At this stage, the color is Moderate Red 2.5R4/10 to Dark Red 2.5R3/7, according to the Nickerson Color Fan, which is used throughout this specification to identify colors and shades which are not sufficiently distinguished by their more common names.

As the calyx breaks the color is generally Dark Red 2.5R3/7.

As the first petals open, the bud is medium to large, relatively long, and pointed to urn-shaped in form. Its outside color is between Moderate Red 2.5R4/10 and Strong Red 2.5R5/12, except for a very small area around the point of attachment, which is near Brilliant Greenish-Yellow 7.5Y9/8. Within the bud, the coloration varies between Strong Red 2.5R5/12 and Strong Red 5R4/12, and is influenced by a fugitive overlay of a color near to Strong Reddish Orange 7.5R5/13. There is a small area at the base, which may sometimes follow the midrib upwards for about half of its length, which is Brilliant Greenish-Yellow 7.5Y9/8. The bud opens up well.

*Bloom*

When the flower is fully open the blooms are medium to large in size, ranging between 3½″ and 4″, and occasionally slightly larger. The petalage is double, but the stamens are not hidden. The bloom will have from forty to fifty petals, and from three to twelve petaloids. These petals are generally arranged regularly, except right at the center, where irregularly-shaped petaloids deviate from the regular placement pattern of the petals. The flower is high-centered at first and at maturity, except that it may become more open at it matures. The petals are slightly rolled outward at first, and this characteristic becomes more accentuated towards maturity.

*Petals*

The petals are relatively thick and leathery, with satiny interior and shiny to satiny exterior. The outer petals are generally broader than long, showing an acute apex with two notches. The intermediate petals are obovate in form, each with an acute apex. The inside petals are obovate to cuneate in form, and are scalloped irregularly with the apex having two notches.

The following description of a flower newly opened in March, refers to a rose grown in a greenhouse in Chino, Calif.

The outer surface of the outside petals displays a small rounded area at the base about ¼" in diameter which is Brilliant Greenish Yellow 7.5Y9/8. The remainder of the outer surface is between Strong Purplish Red 10RP5/12 and Strong Purplish Red 10RP4/12. The inner surface of the outside petals manifests a similar area of Brilliant Greenish Yellow 7.5Y9/8 at the base which sometimes follows the midrib almost to the apex on one or two petals, but the remainder of the inner surface is between Strong Purplish Red 10RP5/12 and Strong Red 2.5R5/12, sometimes with a fugitive overlay of Vivid Red 5R5/13.

The intermediate petals, both on their inner and outer surfaces, likewise display a basal coloration of Brilliant Greenish Yellow 7.5Y9/8, but this occupies a smaller area, being about ⅛" in diameter. The remaining outer surface of the intermediate petals is between Strong Purplish Red 10RP5/12 and Strong Red 2.5R5/12, whereas the inner surface of the intermediate petals varies from Strong Red 2.5R5/12 (which is more dominant at the apex) and Vivid Red 5R5/13 towards the base.

With respect to the inner petals, the Brilliant Greenish Yellow coloration at the base is restricted to a very small area, both on the inner and outer surfaces of the inside petals. The outer surfaces of the inner petals range from Strong Purplish Red 10RP5/12 to Strong Red 2.5R5/12, while the inner surface of the inner petals range from Strong Red 2.5R5/12 towards the apex to Vivid Red 5R5/13 towards the base.

The following description was made from a rose that was open for three days in a greenhouse during the month of March at Chino, Calif.

The outer surface of the outer petals displays an area about ¼" in diameter near the base, which is near white in color, but faintly yellowed. The remainder of the surface is between Strong Purplish Red 10RP4/12 and Strong Purplish Red 7.5RP4/11. The inner surface of the outside petals likewise displays a small area which is nearly white at the base, sometimes following the midrib almost to the apex on one or two petals. The remainder of the inner surface of the outside petals is between Strong Purplish Red 10RP4/12 and Strong Purplish Red 10RP5/12, except for a faint overlay of Strong Red 2.5R5/12 on the veins.

The outer surface of the inside petals shows a similar near white coloration at the base, but of smaller diameter, while the remainder of the surface is between Strong Purplish Red 10RP5/12 and Strong Purplish Red 7.5RP5/12. The inner surface of the inside petals shows the same near white area adjacent to the base, with the remaining surface of the petals between Deep Purplish Pink 7.5RP6/12 near the base ranging to a coloration between Deep Pink 2.5R6/11 and Strong Red 2.5R5/12 at the upper portion of the petal.

The general color effect of the flower is that of Strong Red 2.5R5/12 at the outer circumference when the flower is newly opened, ranging to a color near Vivid Red 5R5/13 in the central portion. After three days the overall color effect is between Deep Pink 2.5R5/11 and Strong Red 2.5R5/12.

Cut roses grown in a greenhouse and kept at living room temperatures persisted for six days in the month of March. The petals drop off cleanly.

*Reproductive organs*

Stamens: Medium to many, often 100 or more, arranged regularly about the pistils, and mixed with the petaloids.

Filaments: Short to medium length, bright yellow at the base and pink to red towards the apex, most of them carrying anthers.

Anthers: Rather small for this class of rose, yellow in color, all opening at once.

Pollen: Moderately abundant and gold in color.

Pistils: Medium to many in number.

Styles: Very uneven, of medium length and thin caliper, bunched and somewhat crimped.

Stigma: Whitish buff.

Ovaries: Enclosed in calyx, but some protruding therefrom.

Hips: More or less globular in shape with thick fleshy walls. They are moderately smooth, and are yellow at maturity.

Sepals: Permanent or nearly so, moderately short in length, fairly straight and spear-shaped in form. They are not significantly colored.

Seeds: Medium size, and ranging from five or six to thirty in number.

*Plant*

Foliage.—The leaves, which are somewhat sparse in number, are compound in form, having three, five or seven leaflets. They range from medium to large size and are relatively rather heavy and leathery. The leaflets are of broadly ovoid shape, with acute apex and an almost round base. The margins are simply serrate, and are slightly rolled downward. The upper surface of the mature leaf is a normal green in color and the undersurface a normal grey-green at maturity. The upper surfaces of the young leaves are a deep purplish-red, more intense than any color swatch on the Nickerson Color Fan. The undersurface of the young leaf is a normal yellowish-green color, but has a heavy overlay of deep purplish-red.

The supporting stem, or rachis, for the compound leaf is of medium weight and is grooved on its upper side, the ridges being moderately lined with fine stipitate glands. The undersides are moderately prickly, usually carrying from two to four prickles. The stipules are of medium length and very narrow; they carry short points which turn out at an angle of about 90°.

This new variety shows better than average resistance to powdery mildew when grown in a greenhouse, as compared with many varieties presently available in commerce, and raised under comparable conditions.

*Growth*

The plant is tall and bushy in habit, upright and much branched. The growth is very vigorous. The canes are of heavy caliper. The main stems are a dull greenish-brown and carry many large prickles which are long, slightly hooked downward, and have long broad bases. The large prickles are grey-brown in color, and this is likewise true of the small prickles, which are quite numerous. There are no hairs. The branches are dull yellowish-green, and carry many large prickles which are long and straight with medium-long broad bases. Both the large and small prickles are numerous, but the branches have many brown hairs.

The new shoots are generally green, with a red overlay. They carry many large prickles which are long and are hooked slightly downward with medium-long broad bases. These large prickles are green at the tip, but red at the base. The small prickles, which are likewise numerous, are reddish in color, and many reddish hairs are present.

We claim:

1. The new variety of rose plant, substantially as herein shown and described, said plant being characterized by its vigorous habit of growth and abundant flower production, as well as by the stiff erect character of the stems and neck, the quantity of small prickles on the peduncle, the large size of the prickles on the canes and branches, and the rolled-down margins of the leaflets; the flower of said plant being further characterized by its distinctive two-tone orange-red color, its high-centered form, and the abundance of its petals.

No references cited.

ROBERT E. BAGWILL, *Primary Examiner.*